(12) United States Patent
Forlin et al.

(10) Patent No.: US 7,981,951 B2
(45) Date of Patent: Jul. 19, 2011

(54) PROCESS FOR PRODUCING EPOXIDES FROM OLEFINIC COMPOUNDS

(75) Inventors: Anna Forlin, Vigonza (IT); Massimo Bergamo, Stade (DE); Wells Carter, Pearland, TX (US); David Jean, Friendswood, TX (US)

(73) Assignee: Dow Global Technologies LLC

( * ) Notice: Subject to any disclaimer, the term of this patent is extended or adjusted under 35 U.S.C. 154(b) by 227 days.

(21) Appl. No.: 12/304,924

(22) PCT Filed: Jun. 19, 2007

(86) PCT No.: PCT/US2007/014246
§ 371 (c)(1),
(2), (4) Date: May 5, 2009

(87) PCT Pub. No.: WO2008/002416
PCT Pub. Date: Jan. 3, 2008

(65) Prior Publication Data
US 2010/0029848 A1     Feb. 4, 2010

Related U.S. Application Data

(60) Provisional application No. 60/816,292, filed on Jun. 23, 2006.

(51) Int. Cl.
| C08L 63/00 | (2006.01) |
| C08G 59/20 | (2006.01) |
| C08G 59/22 | (2006.01) |
| C08G 59/24 | (2006.01) |
| C07D 301/12 | (2006.01) |
| B32B 27/38 | (2006.01) |

(52) U.S. Cl. ........ 523/403; 523/400; 523/402; 549/518; 549/523; 549/524; 549/531

(58) Field of Classification Search .......... None
See application file for complete search history.

(56) References Cited

U.S. PATENT DOCUMENTS

| 3,956,309 | A | 5/1976 | Habermeier et al. |
| 4,562,276 | A | 12/1985 | Venturello et al. |
| 4,595,671 | A | 6/1986 | Venturello et al. |
| 4,973,718 | A * | 11/1990 | Buchler et al. ............... 549/531 |
| 5,274,140 | A | 12/1993 | Venturello et al. |
| 5,767,150 | A | 6/1998 | Fan et al. |
| 6,080,872 | A | 6/2000 | Pirola et al. |
| 6,194,490 | B1 | 2/2001 | Roth et al. |
| 6,255,500 | B1 | 7/2001 | Klemarczyk |
| 6,372,924 | B2 * | 4/2002 | Thiele ............... 549/531 |
| 6,420,575 | B1 | 7/2002 | Ninomiya et al. |
| 6,774,250 | B1 | 8/2004 | Hatton et al. |
| 2006/0194063 | A1 | 8/2006 | Murai et al. |
| 2007/0093667 | A1 | 4/2007 | Watanabe et al. |
| 2007/0117993 | A1 | 5/2007 | Hori et al. |

FOREIGN PATENT DOCUMENTS

EP    0 300 163 A    5/1988

OTHER PUBLICATIONS

Venturello C., et al. "Quaternary Ammonium Tetrakis (diperoxotungsto) phosphates (3-) as a New Class of Catalysts for Efficient Alkene Epoxidation with Hydrogen Peroxide." Journal of Organic Chemistry, American Chemical Society. Eston, US. vol. 53, No. 7, 1988, pp. 1553-1557.
Teshigahara, S., et al., Epoxidization of Alicyclic Olefin, JP5213919A, Abstract.
Nobukatsu, I., Device for Lining Inner Surface of Pipe by Air Floating Method, JP62234570A, Abstract.
Bull, A., et al., Epoxidation of Cyclohexene Compounds, Equivalent of JP62230778, Abstract of Equivalent ES2003695A6.

* cited by examiner

*Primary Examiner* — Michael J Feely

(57) ABSTRACT

A process for producing an epoxide such as a cycloaliphatic diepoxide by the reaction of an olefin such as a cycloaliphatic diene with hydrogen peroxide ($H_2O_2$) as an oxidant in the presence of a catalytic system under pH control for example at a pH of less than about 5. The present invention is advantageously used for the epoxidation of olefinic compounds such as olefins and aliphatic or aromatic dienes.

21 Claims, No Drawings

PROCESS FOR PRODUCING EPOXIDES FROM OLEFINIC COMPOUNDS

CROSS REFERENCE TO RELATED APPLICATIONS

This is a §371 application of PCT International Patent Application Number PCT/US2007/014246 filed Jun. 19, 2007, and claims priority from provisional application serial number 60/816,292 filed Jun. 23, 2006, each of which is incorporated herein by reference in its entirety.

The present invention relates to a process for epoxidizing epoxidizable olefinic compounds under phase-transfer catalysis conditions. More specifically, the present invention relates to a process for producing an epoxide by reacting olefinic compounds including olefins and aliphatic or aromatic dienes with hydrogen peroxide ($H_2O_2$) as an oxidant in the presence of a transition metal catalyst. Even more specifically, the process of the present invention is advantageously used for the epoxidation of a cycloaliphatic diene to form a cycloaliphatic diepoxide. The epoxide products of the present invention are useful as intermediates in the production of other products for example suitable for use in the fields of coatings, laminates, composites, encapsulations, and molding compositions.

It is generally known to epoxidize unsaturated olefinic compounds using various peroxy compounds as oxidants such as peracidic acid and hydrogen peroxide in the presence of a phase transfer catalyst. For example, a process for the epoxidation of aliphatic diene esters, including cycloaliphatic diene esters, using a peracid such as peracetic acid as an oxidant is disclosed in U.S. Pat. No. 6,255,500.

However, the known processes using peracidic acid are complex, require a great amount of maintenance, use a high corrosive medium, are not cost-efficient and are very energy intensive. For the known processes of producing cycloaliphatic epoxides that use peracetic acid as an oxidant agent, the majority of product is at a high yield because the product includes oligomers as part of the product. Typically, the concentration of oligomers in the product is 10 percent by weight or greater.

It would be advantageous to the industry to provide a new process that is easier to run without the need of peracidic acid. It would be desirable to provide a new process which is not energy intensive, not expense and does not require a lot of maintenance. It would also be beneficial to provide a new process which produces a new product with a lower viscosity without having to further process the product such as by distillation. It is desired to produce such a product having a lower viscosity and good flexibility.

The process of epoxidizing an olefin compound with hydrogen peroxide is also generally known. For example, a process for the catalytic epoxidation of olefins by reaction with hydrogen peroxide as the oxidizing agent is disclosed in U.S. Pat. No. 5,274,140; PCT WO 98/27099 A2; and Japanese Unexamined Patent Publications No. 5-213,919, No. 62-230,778, and No. 62-234,570. These prior art processes do not provide for pH control of the reaction mixture to obtain a high product yield.

It is desired to provide a process for the catalytic epoxidation of epoxidizable olefinic compounds such as cycloaliphatic dienes via an oxidizing agent such as $H_2O_2$ wherein the process is simple and cost-efficient and provides a corresponding epoxide product in excellent yield and purity.

It is desired to provide a process which is simple, straightforward and relatively inexpensive that can be carried out in large scale runs to produce commercially useful quantities of pure reaction product.

One aspect of the present invention is directed to a novel process for preparing epoxides, such as cycloaliphatic epoxides, wherein the process uses aqueous $H_2O_2$ as an oxidant agent plus a phase transfer catalyst to epoxidize an olefinic compound to an epoxide such for example a cycloaliphatic diene to cycloaliphatic epoxides. The epoxidation is conducted in a way to control the pH of the reaction medium such as for example by addition of a buffer solution to the reaction medium. Under the process conditions of the process of the present invention, there is a yield improvement of more than 50 percent for example to cycloaliphatic epoxide with low formation of heavy by-product.

Use of an aqueous $H_2O_2$ in the process of the present invention provides a high purity product with a low amount of oligomers. The process of the present invention also provides an overall high yield related to diene, close to 100 percent. The use of a pH control agent, for example a buffer solution, in the present invention provides surprising high epoxidation yield with a cycloaliphatic diene as a starting substrate.

Another aspect of the present invention is directed to a composition comprising the diepoxide of a diene containing a monoepoxide of a diene wherein the (percent) monoepoxide in the composition is less than about 10 percent by weight of the total product; wherein the content of the OH-terminated by-products in the composition is less than about 8 percent by weight; and wherein the composition has a low product viscosity and other beneficial properties such as good flexibility.

The process of the present invention for the epoxidation of an olefinic compound such as a diene includes (a) reacting an olefinic compound with $H_2O_2$ as an oxidant at a temperature of from 10° C. to 100° C., in the presence of a catalyst; and, optionally in the presence of a pH control buffer solution; to epoxidize the double bonds of the olefinic compound; and (b) isolating the epoxidized olefinic compound from the resulting reaction mixture.

The olefinic compound used as a starting material in the reaction of the present invention may be any olefin that has unsaturated bonds. The olefin contains at least one double bond; and may contain two or more double bonds such as dienes or olefins with multiple double bonds. The double bond(s) may be internal or terminal. The olefin may have from $C_6$ to $C_{18}$ carbon atoms and may be an aliphatic, a cyclic, or an aromatic compound. Preferably, the olefin is a compound that does not contain a nitrogen element. The process of the present invention is advantageously used with olefin starting materials that are sensitive to pH and requires controlling the pH of the reaction medium to obtain an epoxide product therefrom. In one embodiment, the process of the present invention produces an epoxide wherein at least 95 percent of the double bonds in the olefin starting material are converted to an epoxide.

The olefin useful in the present invention may include for example fatty triglycerides acids (linseed oils, soybean oil and other natural oils), $C_6$-$C_{18}$ alfa and internal olefin, etc.). Soybean oil is the random mixture of the triglycerides (esters of fatty acids with glycerine, a trifunctional alcohol) provided by mother nature in the soybean. Soybean oil has the following average structure rich in the polyunsaturated (many double bonds) fatty acids that cholesterol-conscious dieters prefer:

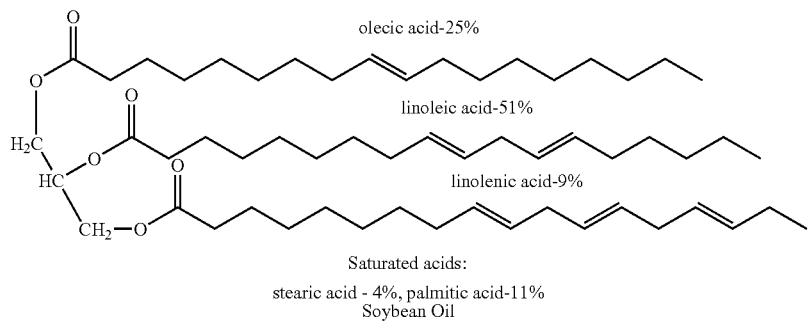

Soybean Oil

Linseed oil is produced from the flaxseed byproduct of the linen textile industry. Linseed oil is a polyunsaturated oil consisting of a random mixture of fatty acid triglycerides with the following average structure, which is particularly rich in the triply unsaturated linolenic acid:

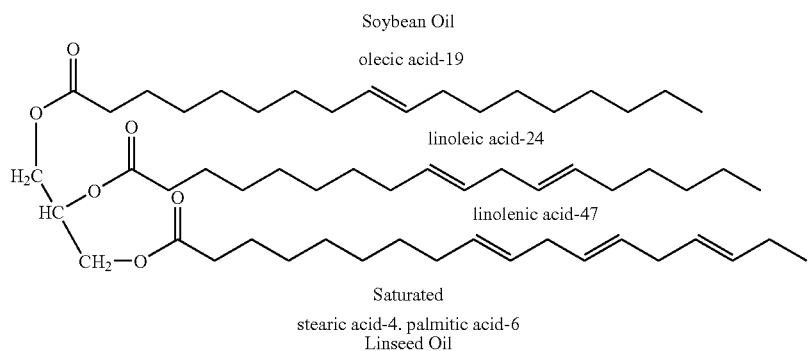

Linseed Oil

Tall oil and the fatty acids derived from tall oil (predominantly oleic and linoleic acid) are byproducts of the Kraft paper wood pulping process. These byproducts result from sulfuric acid catalyzed hydrolysis of the fats originally present in the wood used to make paper pulp.

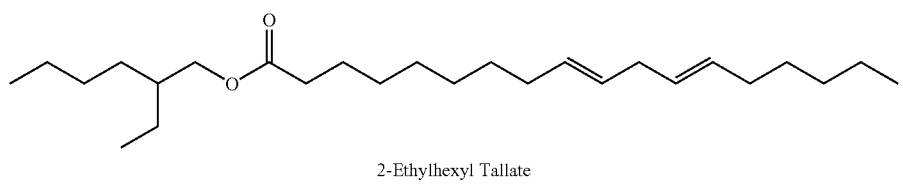

2-Ethylhexyl Tallate

By esterification of tall oil fatty acid with tetra-alcohol pentaerythritol the following structure is obtained:

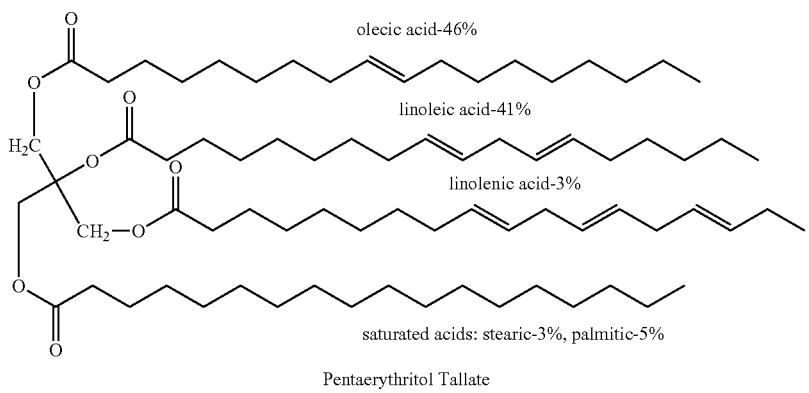

Pentaerythritol Tallate

The olefins employed in the present invention are preferably aliphatic dienes. Various aliphatic dienes that can be used in the practice of the present invention include for example 3-cyclohexene-1-carboxylic acid, 3-cyclohexen-1-ylmethyl ester ("Diene 221") [Formula IA]; hexanedioic acid, bis(3-cyclohexen-1-ylmethyl)ester [Formula IIA]; cyclohexane, 4,4'-(1-methylethyldiene)bis[Formula IIIA]; vinylcyclohexene(VCH) [Formula IVA]; tripropylene glycol, 3-cyclohexenecarboxylic diester [Formula VA]; cyclohexyl-1,4-bis(methyl 3-cyclohexenecarboxylate [Formula VIA]; cyclohexyl-1,4-bis(methyl 3-cyclohexenecarboxylate mixed with 1,3- and 1,4-isomers prepared using mixed isomers 1,3- and 1,4-cyclohexanedimethanol [Formula VIIA]; 3-cyclohexene-1-carboxylic acid methyl ester [Formula VIIIA]; 2-ethylhexanoic 3-cyclohexenecarboxylate [Formula IXA]; and mixtures thereof. Preferably, the olifen employed in the present invention is Diene 221.

The chemical structures of the dienes used as starting material for the process of the present invention are shown in Formulas IA-1×A and their corresponding epoxide is shown in Formulas IB-IXB, respectively, as follows:

Formula IA

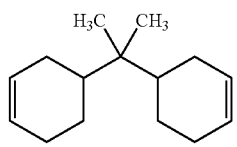

Formula IB

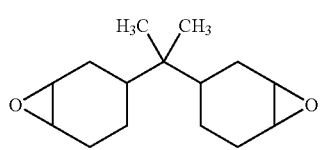

Formula IIA

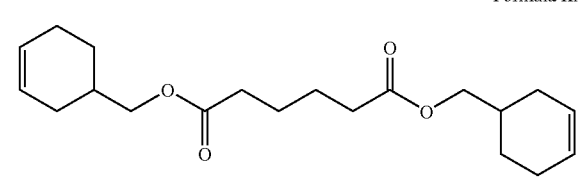

Formula IIB

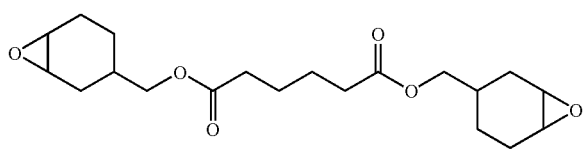

Formula IIIA

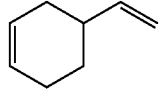

Formula IIIB

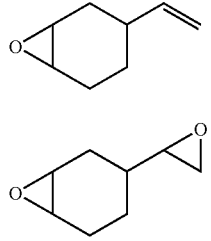

Formula IVA

Formula IVB1

Formula IVB2

Formula VA

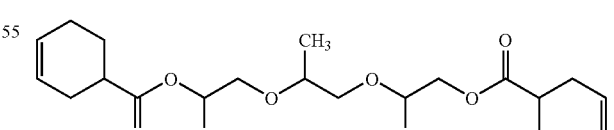

Formula VB

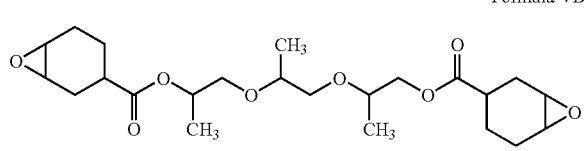

Formula VIA

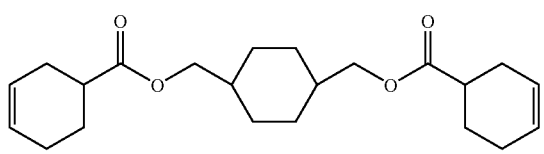

Formula VIB

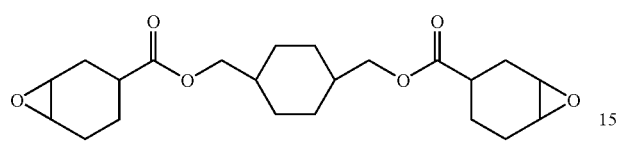

Formula VIIA

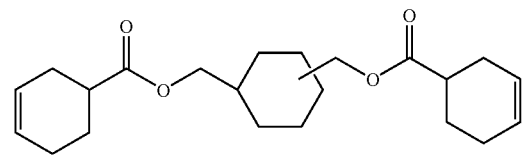

Formula VIIB

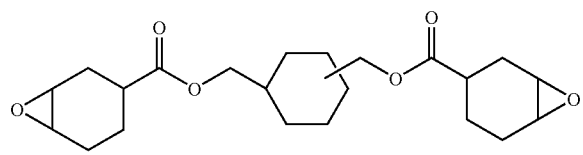

Formula VIIIA

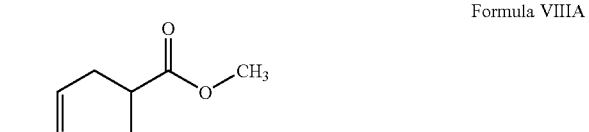

Formula VIIIB

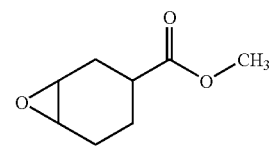

Formula IXA

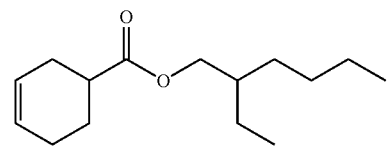

Formula IXB

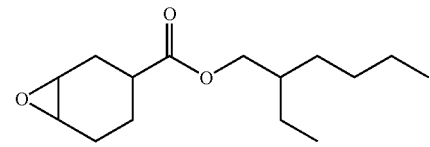

Preferably, the aliphatic diene used in the present invention as the starting material is a cycloaliphatic diene having the following formula:

FORMULA IA

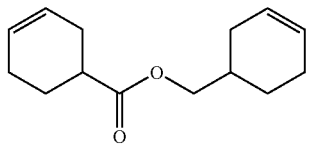

The corresponding epoxidized material, the diepoxidized diene, resulting from the epoxidation of the diene of FORMULA IA above has the following formula:

FORMULA IB

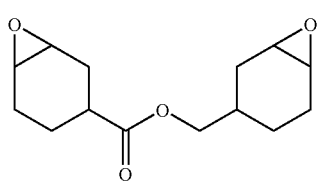

Particularly desirable epoxide compounds with FORMULA IB above that are prepared by the process of the present invention include an epoxide product having a content of less than about 10 percent by weight (wt percent) of a monoepoxide, and preferably less than about 8 wt percent. The preferred compounds of FORMULA IB include for example, epoxides having a monoepoxide content of from 3 wt percent to 10 wt percent and preferably from 3 wt percent to 7 wt percent. In one embodiment, the process of the present invention produces an epoxide wherein the percent monoepoxide in the resulting epoxide product ranges from 3 percent to 10 percent by weight of the total epoxide product.

The following monoepoxides and their isomers may be formed during the epoxidation process:

FORMULA IC

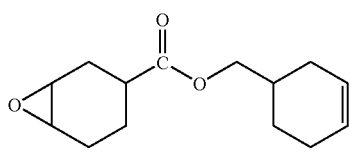

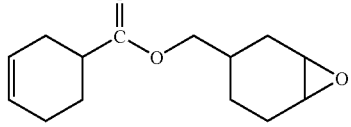

Monoepoxide Isomers: MW 236

Typically, the above monepoxides isomers have a molecular weight of about 236.

Aqueous hydrogen peroxide ($H_2O_2$) of the present invention is the preferred peroxy compound that is used in carrying out the epoxidation reaction of the present invention. Hydrogen peroxide, due to its oxidizing action associated with the absence of environmental problems, problems with pollution, etc. makes $H_2O_2$ a suitable oxidizing agent for the epoxidation process of the present invention. The aqueous $H_2O_2$ is commercially available in wide range of concentrations for example from 5 wt percent to 70 wt percent. The amount of hydrogen peroxide used in the present invention comprises from 0 percent to 20 percent stoichiometric excess above the theoretical amount required for complete epoxidation of the double bonds of the olefin compound being epoxidized.

In the epoxidation reaction mixture of the present invention, the hydrogen peroxide (on a 100 percent basis) is generally employed in an amount of from 1 wt percent to 20 wt percent, preferably from 4 wt percent to 16 wt percent, and more preferably from 8 wt percent to 12 wt percent.

The epoxidation reaction of the present invention is preferably carried out in the presence of a phase transfer catalyst. The catalyst preferably contains a transition metal. The compounds useful for the epoxidation catalyst for the epoxidation reaction of the present invention are preferably selected from homogeneous and heterogeneous catalysts based on metals, such as Ti, Re, Mo, V, W and Mn, preferably W/oxo/peroxo complexes. The catalyst is preferably an amphiphilic quaternary ammonium peroxo tungstophosphate. The catalyst used in the present invention may be the catalyst described in Journal of Organic Chemistry (1988), 53, pp 1553-1557; U.S. Pat. Nos. 4,562,276; 4,595,671 and 5,274,140; and European Patent Application EP 1170 291 A1.

The catalyst useful in the present invention may be in the form of a solid prepared in accordance with the process described in the above Journal of Organic Chemistry; or the catalyst may be in the form of a liquid composition as described in EP 1170 291 A1.

For example, the catalyst used in the present invention may be the catalytic system described in EP1170 291A1 which includes a composition comprising a tungsten compound, a quaternary onium salt and a mineral acid.

The tungsten compounds usable for the epoxidation catalyst for the epoxidation reaction may be selected from inorganic acids containing tungsten atoms and salts thereof. The tungsten atom-containing acids and salts thereof include, for example, tungstic acid (wolframic acid) and salts thereof, for example, sodium tungstate, potassium tungstate, lithium tungstate, ammonium tungstate; and dodecatungstates, for example, sodium dodecatungstate, potassium dodecatungstate and ammonium dodecatungstate; and heteropoly-acids and salts thereof, for example, phosphotungstic acid, sodium phosphotungstate, silicotungstic acid, sodium silicotungstate, phosphovadadotungstic acid; and phosphomolybdotungstic acid, preferably tungstic acid, sodium tungstate, potassium tungstate, and phosphotungstic acid. There tungsten compounds may be employed alone or in a mixture of two or more thereof.

The tungsten compound for the epoxidation reaction of the method of the present invention may be employed in an amount of from 0.0007 wt percent to 5 wt percent, more preferably from 0.002 wt percent to 3 wt percent, in terms of tungsten atoms, based on the amount of the olefinic compound used in the reaction.

In the process of the present invention, the quaternary onium salts usable for the epoxidation catalyst include quaternary ammonium halides, for example, trioctylmethyl ammonium chloride, tridecylmethyl ammonium chloride, trioctylmethyl ammonium bromide, benzyldimethyltetradecyl ammonium chloride, benzyltriethyl ammonium chloride, dimethyldidodecyl ammonium chloride, benzyltributyl ammonium chloride, benzyltributyl ammonium iodide and phenyltrimethyl ammonium chloride; quaternary ammonium hydrogen sulfates; for example, trioctylmethyl ammonium hydrogen sulfate; quaternary ammonium perchlorates, for example, trioctylmethyl ammonium perchlorate; quaternary ammonium dihydrogen phosphates, for example, trioctylmethyl ammonium dihydrogen phosphate; quaternary ammonium nitrate, for example, trioctylmethyl ammonium nitrate; quaternary ammonium hydrosilicofluorate, for example, trioctylmethyl ammonium hydrosilicofluorate; and quaternary ammonium acetates, for example, trioctylmethyl ammonium acetate. Among the above-mentioned quaternary onium salts, preferably quaternary ammonium halides, more preferably trioctylmethyl ammonium chloride and tridecylmethyl ammonium chloride are employed.

The content of the quaternary onium salt in the epoxidation catalyst may be from 0.0003 wt percent to 4 wt percent, and preferably from 0.003 wt percent to 2.5 wt percent, based on the amount in weight of the olefinic compound used in the reaction.

The mineral acids usable for the epoxidation catalyst include, for example, phosphoric acids, sulfuric acids, hydrochloric acid, perchloric acid, hexafluorosilicic acid, nitric acid and tetrafluorosilicic acid. Preferably, phosphoric acid and sulfuric acid, more preferably phosphoric acid, are employed for the epoxidation catalyst. The above-mentioned mineral acids may be employed alone or in a mixture of two or more thereof.

The content of the mineral acid in the epoxidation catalyst may be from 0.001 wt percent to 5 wt percent, and preferably from 0.005 wt percent to 3 wt percent, based on the amount (by weight) of olefinic compound used in the reaction.

More preferably, the catalyst useful in the present invention may be a catalyst as described in J. Org. Chem. 1988, 53, 1553-1557 and illustrated by the following chemical structure:

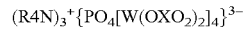

$$(R4N)_3^+\{PO_4[W(OXO_2)_2]_4\}^{3-}$$

where R is a C1-C24 hydrocarbon chain. Some examples for R in the above formula are as follows: $CH_3$; $C_6H_{13}$; $C_8H_{17}$; $C_{16}H_{33}$; and $C_{18}H_{37}$.

And more specifically, some examples of $R4N^+$ in the above catalyst formula are as follows:

a: $[(C_6H_{13})_4N]^+$;
b: $[(C_8H_{17})_3NCH_3]^+$; and
c: $\{[C_{18}H_{37}(76)+C_{16}H_{33}(24)]_2N(CH_3)_2\}^+$.

The catalyst employed in the epoxidation reaction of the present process is preferably type c above and it is employed in an amount of from 0.1 wt percent to 1.5 wt percent, preferably from 0.2 wt percent to 1.2 wt percent, and more preferably from 0.4 wt percent to 1 wt percent.

In the process of the present invention, the epoxidation reaction is preferably carried out in the presence of a buffering agent. The buffering agent is added to the reaction mixture to maintain the reaction mixture at a pH of less than 5 during the epoxidation reaction because for certain olefins, whose epoxides are sensitive to a greater extent to the acid-catalyzed hydrolysis, the reaction is best performed where the pH of the aqueous phase is adjusted to a value suitable to sufficiently prevent the ring opening of the related epoxides. In one embodiment, the process of the present invention is carried out at a pH comprising from 3.5 to 4.5.

The buffering agent preferably comprises a mixture of components including the following three materials mixed together to function in combination as a buffering agent in the present invention: (a) a tungstate material to assist in maintaining the activity of the catalyst; (b) a phosphoric acid also to assist in maintaining the activity of the catalyst; and (c) an alkali metal salt to maintain the pH of the reaction mixture.

Component (a) of the buffering agent may be any of the tungsten compounds described above with reference to the catalyst. Component (a) employed in the epoxidation buffering agent for the epoxidation reaction of the present invention, preferably includes $Na_2WO_4*2H_2O$, $K_2WO_4$, $[(NH_4)_2WO_4$ and mixtures thereof.

Component (a) is used in a molar ratio of from 0:1 to 5:1 Component (a)/catalyst.

Component (b) of the buffering agent may be any of the mineral acids described above with reference to the catalyst. Component (b) employed in the epoxidation buffering agent for the epoxidation reaction of the present invention, preferably includes $H_3PO_4$.

Component (b) is used in a molar ratio of from 0:1 to abut 30:1 Component (c)/catalyst.

Component (c) of the buffering agent may be an aqueous alkali solution usable for the process of the present invention. The aqueous solution may be at least one member selected from basic organic compounds of alkali metals and alkaline earth metals and ammonia. The aqueous alkali solution has a pH value of more than 7, preferably 8 or more, more preferably 10 or more, still more preferably 11 or more. The basic organic compound includes hydroxides of alkali metals, carbonates of alkali metals, bicarbonates of alkali metals, sulfites of alkali metals, hydroxides of alkaline earth metals, carbonates of alkaline earth metals, bicarbonates of alkaline earth metals and sulfites of alkaline earth metals. Preferably, the hydroxides of alkali metals, carbonates of alkali metals, bicarbonates of alkali metals and sulfites of alkali metals are employed and more preferably the hydroxides of alkali metals are employed.

Practical examples of the alkali metal hydroxides and alkaline earth metal hydroxides are potassium hydroxide, sodium hydroxide, magnesium hydroxide, barium hydroxide and calcium hydroxide.

Practical examples of the alkali metal carbonates and alkaline earth metal carbonates are potassium carbonate, sodium carbonate, magnesium carbonate and calcium carbonate.

Practical examples of the alkali metal bicarbonates are potassium bicarbonate and sodium bicarbonate. Practical examples of the alkali metal sulfites are potassium sulfite and sodium sulfite.

Preferably, sodium hydroxide, potassium hydroxide and sodium sulfite, more preferably sodium hydroxide and potassium hydroxide are employed. The above-mentioned alkali metal compounds and alkaline earth metal compounds and alkaline earth metal compounds may be employed alone or in a mixture of two or more thereof.

Component (c) employed in the epoxidation buffering agent for the epoxidation reaction of the present invention, preferably includes NaOH, KOH, $NH_4OH$ and mixtures thereof.

Component (c) is used in an amount sufficient to obtain a pH of the aqueous phase of about 4. Component (c) is used in a molar ratio of from 5:1 to 20:1 Component (c)/catalyst.

The buffering agent advantageously allows the process to proceed as desired. Components (a) and (b) are added to maintain the catalyst active. Component (c) is used to maintain the pH at about 5 or less.

The buffering agent of the epoxidation reaction of the present process is employed in an amount sufficient to maintain the pH of the reaction mixture at about 5 or less and to maintain the reactivity of the catalyst. The buffering agent provides the reaction mixture with a pH of generally less than 5 and preferably from 3.5 to 4.5.

Optionally, the epoxidation reaction of the present invention may be advantageously carried out in an inert solvent. Suitable inert solvents that may be useful in the present process include for example, alkyl esters, halogenated hydrocarbons, cycloaliphatic hydrocarbons, aromatic hydrocarbons, alcohols and mixtures thereof. More specifically, one or more solvents useful in the present invention may include, benzene, toluene and aromatic solvents, dichloromethane, dichloromethane and chlorinated solvents, hexane, cyclohexanone, aliphatic and cycloaliphatic alkenes, alcohols, ethers, halogenated and nitrogenated solvents and mixtures thereof.

When a solvent is used in the reaction process of the present invention, the amount used based on the overall reaction mixture, is generally in the range of from 0.0001 wt percent to 90 wt percent, preferably from 0.5 wt percent to 60 wt percent, and more preferably from 30 wt percent to 50 wt percent.

In the epoxidation reaction in accordance with the process of the present invention, the organic solvent may be contained as a reaction medium in the reaction system. There is no limitation to the type of the organic solvent as long as the organic solvent is not detrimental to the epoxidation reaction. The organic solvent for the reaction medium includes aliphatic halogenated hydrocarbons, for example, chloroform, dichloroethane, and dichloromethane; aliphatic non-halogenated hydrocarbons, for example, cyclohexane and n-heptane; and aromatic hydrocarbons, for example, benzene, toluene and xylene. The above-mentioned organic solvents may be employed alone or in a mixture of two or more thereof.

When the organic solvent is employed, the amount in weight of the organic solvent preferably does not exceed 20 times, and more preferably does not exceeding 10 times, the weight of the olefinic compound.

The epoxide compounds of the present invention are produced by the epoxidation of the olefinic linkages contained in the starting material. Generally, the epoxidation reaction may be conducted in a wide range of reaction conditions. For example, the temperature range of the reaction is generally from 10° C. to 100° C., and preferably between 50° C. and 70° C.

The duration of the reaction depends on the nature and on the quantity of the catalyst, on the solvent medium and on the olefin used in the process. In general, the reaction time can be from minutes to hours for completing the reaction. Preferably, the epoxidation reaction time can range from 1 hour to 20 hours, most preferably between 4 hours and 6 hours. Preferably, the hydrogen peroxide is added to the reaction mixture at a temperature in the range of 10° C. to 100° C. over a period of from 1 minute to 300 minutes.

The pressure range of the epoxidation reaction is generally from vacuum to 30 atmospheres (atm), most preferably between 1 atm and 5 atm.

The order of addition of the starting materials is not critical and can be carried out in any order. Preferably the mixing is carried out in the following order: first, the toluene and the catalyst (as a solid, as a solvent solution, or as catalyst components separately) are added into the reactor; then the diene is added to the reactor; and then the $H_2O_2$/buffering agent is added to the reaction mixture. The reaction mixture is thoroughly mixed under vigorous mixing conditions.

The reaction may be carried out under an inert gas atmosphere such as nitrogen.

Preferably, the epoxidation reaction is carried out in a two liquid phase system consisting of a liquid phase comprising the olefinic compound and another liquid phase comprising the aqueous hydrogen peroxide solution, phase-separated from each other. For example, the epoxidation reaction is carried out by vigorously mixing the olefinic compound, an aqueous hydrogen peroxide solution and a catalyst comprising a transition metal compound with each other in an atmosphere that may consist of an inert gas for example, nitrogen gas, and by heating the resultant mixture under an ambient atmospheric pressure or an increased pressure, while thoroughly agitating the mixture. There is no limitation to the reaction temperature. As mentioned above, usually, the reaction temperature is generally from 10° C. to 100° C., and preferably from 50° C. to 70° C.

The preferred method of making the epoxides includes mixing the starting materials and hydrogen peroxide and reacting at a temperature of from 50° C. and 70° C. After completion of the reaction, the product may be recovered by any convenient means known to those skilled in art, such as, for example, distillation or extraction. The catalyst may also be separated from the reaction by well known means in the art.

As an illustration of one embodiment of the process of the present invention, the process is conducted using a reactor fitted with a stirrer, a heat-controlling system and a reflux coolant. Pre-established quantities and ratios of the reactants ($H_2O_2$ and the olefin in the solvent) are introduced into the reactor. The catalyst and buffering agent is also introduced into the reactor in the desired quantities. Under vigorous stirring, the heterogeneous mixture is brought to the reaction temperature for the desired time. At the end of the reaction time, the reaction mixture separates into two phases. After cooling down of the reaction phases, the epoxide and the reactants may be separated by conventional means and methods such as distillation or extraction. Isolating the epoxidized product from the resulting reaction mixture can be carried out by any technique well known to those skilled in the art, and the present invention is not limited to any particular method for isolating the reaction product from the reaction mixture.

The process of the present invention provides high yields, for example preferably higher than 90 percent; and high selectivity for example preferably higher than 90 percent of product that makes the process attractive for the industrial application of the process.

The epoxidation process of the present invention provides a product with advantageous properties, particularly when using the epoxide product for various end uses. For example, the epoxide product has a viscosity in the range of from 150 centipoises (cps) to 350 cps, preferably from 220 cps to 320 cps, and more preferably from 230 cps to 310 cps at 25 ° C. Also, the product has a percent (percent) by weight (wt) monoepoxide content of from 0 wt percent to 15 wt percent based on the total product, preferably from 2 wt percent to 10 wt percent and more preferably from 3 wt percent to 7 wt percent; and a content of OH-terminated by-products of for example in the range of from 0 wt percent to 10 wt percent, preferably from 2 wt percent to 8 wt percent and more preferably from 3 wt percent to 7 wt percent. In one embodiment, the process of the present invention produces an epoxide product containing an acetate content of less than about 10 ppm. In another embodiment, the composition of the present invention comprising a diepoxide has a viscosity of less than 350 cps at 25 ° C.

The OH-terminated by-products are oligomer molecules that still have unreacted epoxide groups. The monomer component is a monoepoxide, the dimer component is a diepoxide, the trimer is a triepoxide, etc. as illustrated by the general oligomeric structure in Formula (X). For example, the monomer structure of Formula (X) is when n=0 [Formula X(A)], and the dimer structure is when n=1 [Formula X(B)] as shown below:

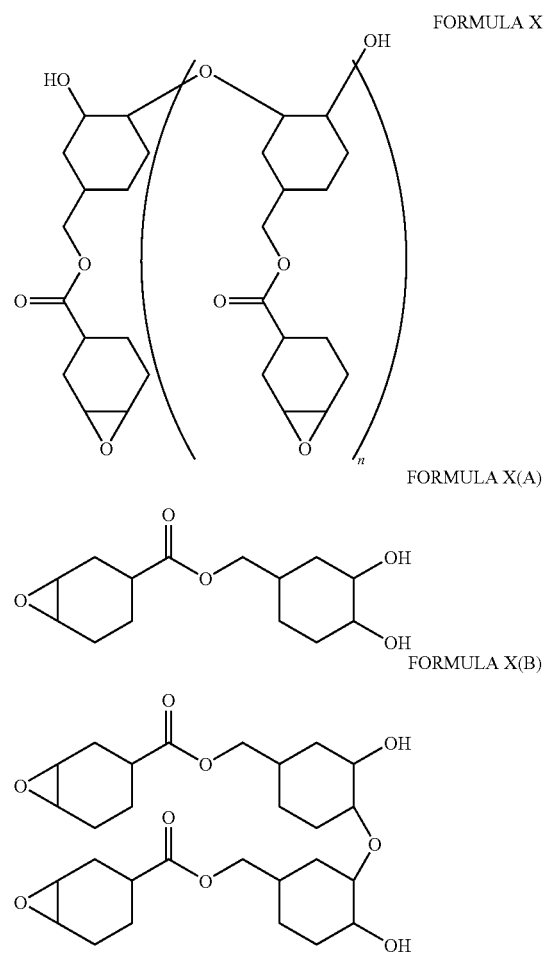

The oligomers of Formula X present in the final product may be oligomers of multiple monomer units wherein n can be from 0 to 6.

The resulting product of the present invention has good properties including excellent flexibility. Flexibility is measured by the wedge bend retort method.

The retort wedge bend method is carried out by bending a coated metal panel sample, for example a coated steel panel, using a wedge bend instrument and then placing the sample in an autoclave. The autoclave contains water and is operated at about 121° C. for 1 hour. The temperature generates steam and about 14 pounds per square inch (psi) pressure. The temperature and the steam affect the coating and rust exposed steel. Coatings are observed and those that are cracked/pitted along the entire length of bend are failures with the worst failure being along the most severe bend with fewer pits observed along the less severe bend.

The good properties of the product make the product useful in compositions which need improved toughness, for example.

As an illustration of a typical product of the present process, the product may contain, for example, the following components:

| | 7 percent [monoepoxy/ (monoepoxy + diepoxide)] Gas Chromotography (GC) Area | 3 percent[monoepoxy/ (monoepoxy + diepoxide)] Gas Chromotography (GC) Area |
|---|---|---|
| Diepoxide | 89.6 | 91.8 |
| Monoepoxide | 6.6 | 2.7 |
| Low MW By-products | 3.1 | 3.1 |
| High MW By-products | 0.7 | 2.5 |
| Total By-products | 3.8 | 5.5 |

The final product may have, for example, a low molecular weight by-product such as a product having a molecular weight (MW) of 270; and for example, a high molecular weight by-product such as a product having a MW of 522; and other higher MW by-products.

The epoxide products prepared by the process of the present invention are useful as intermediates in the production of products suitable for use in the fields of coatings, inks, adhesives, laminates, composites, potting, encapsulating, and molding compositions.

The epoxidized product prepared by the process of the present invention is useful as one component in a curable epoxy resin composition wherein the epoxy compound is reacted with a curing agent, together with other typical ingredients, for curing the resin composition to provide thermosets for the various end uses mentioned above. The curable epoxy resin composition containing the epoxy compound can also contain one or more additional epoxy compounds, solvents, catalysts, plasticizers, fillers, pigments and/or any other commonly used additives for the application being employed.

The epoxy compounds prepared according to the present invention can be used alone or in combination with other epoxy compounds to manufacture cured epoxy resins by reacting the epoxy compound(s) with well known epoxy curing agents. Such curing agents include, for example, amine-curing agents such as dicyandiamide, diaminodiphenylmethane and diaminodiphenylsulfone; anhydrides such as hexahydroxyphthalic anhydride and styrene-maleic anhydride copolymers; imidazoles; and phenolic curing agents such as phenol novolac resins; and mixtures thereof. Such curing agents can be added to a resin composition immediately before curing, or can be included in the composition from the beginning if the curing agents are latent. The amount of the curing agent used may normally range from 0.3 to 1.5 equivalent per epoxy equivalent of the epoxy components, and preferably from 0.5 to 1.1 equivalent per epoxy equivalent of the epoxy components.

Preferably, the curing agent may include for example tetrahydrophthalic anhydride (THPA), methyl tetrahydrophthalic anhydride (MTHPA), hexahydrophthalic anhydride (HHPA), methyl hexahydrophthalic anhydride (MHHPA), nadic methyl anhydride (NMA), polyazealic polyanhydride, succinic anhydride, maleic anhydride, phthalic anhydride, and mixtures of anhydrides.

More preferably, the curing agent used in the present invention may be methyl tetrahydrophthalic anhydride (MTHPA), hexahydrophthalic anhydride (HHPA), and methyl hexahydrophthalic anhydride (MHHPA). In one embodiment, the process of the present invention for preparing a curable epoxy resin composition is carried out wherein the curing agent is selected from the group consisting of methyl tetrahydrophthalic anhydride (MTHPA), hexahydrophthalic anhydride (HHPA), and methyl hexahydrophthalic anhydride (MHHPA).

A typical epoxy resin composition containing the epoxide compound prepared by the process of the present invention may also comprise, as an optional component, catalysts for catalyzing the reaction of the epoxy compound and the curing agent. Examples of the suitable catalysts are imidazoles such as 2-methylimidazole; 2-phenyl imidazole and 2-ethyl-4-methyl imidazole; tertiary amines such as triethylamine, tripropylamine and tributylamine; phosphonium salts such as ethyltriphenylphosphonium chloride, ethyltriphenylphosphonium bromide and ethyltriphenylphosphonium acetate; and ammonium salts such as benzyltrimethylammonium chloride and benzyltrimethylammonium hydroxide, and mixtures thereof.

Cationic photoinitiators, which release an acid when exposed to ultra violet (UV) or electron-beam radiation, may be also used as catalysts for catalyzing reactions of the epoxy compound including for example homopolymerization and reactions of the epoxy compound and other epoxy compounds, oxetanes, and hydroxyls for example. Examples of suitable cationic photoinitiators include aryl sulfonium salts and aryl iodonium salts containing non-nucleophilic anions capable of curing epoxy resins when exposed to UV or electron-beam radiation. The amount of the catalysts used in the present invention generally ranges from 0.001 wt percent to 2 wt percent, and preferably from 0.01 wt percent to 0.5 wt percent, based on the total weight of the reaction mixture. The amount of cationic photoinitiator may vary from 0.001 wt percent to 20 wt percent, and preferably from 0.1 wt percent to 10 wt percent.

Preferably, catalysts may include benzyldimethylamine (BDMA), 1,4-diazabicyclo[2.2.2]octane (DABCO), tertiary amines, imidazole and derivatives of imidazole, 1,8-diazabicyclo[5.4.0]undec-7-ene (DBU), chlorine, benzyl triethyl ammonium chloride, ethyl triphenyl phosphonium iodide, benzyl triphenyl phosphonium bromide, tetraethyl ammonium bromide, Mark DBVIII from Witco, stannous octoate, zinc octoate and including mixtures of these catalysts.

More preferably, the catalyst used in the present invention include benzyldimethylamine, diazabicyclo[2.2.2]octane (DABCO), and imidazole and derivatives of imidazole.

Preferably, cationic photoinitiators include mixed triaryl sulfonium hexafluorophosphate salts, for example CYRACURE UVI-6992, and mixed triaryl sulfonium hexafluoroantimonate salts, for example CYRACURE UVI-6976, products of The Dow Chemical Company; and mixed diaryl iodoinum hexafluorophosphate salts, for example Irgacure 250, product of Ciba Specialty Chemical Company.

Examples of thermally cured compositions wherein the epoxidized product of the present invention is used as one component in a resin composition in significant concentrations include insulators for instrument transformers, switch gear, and bushings; medium voltage power lines insulators; light-emitting diode (LED) encapsulant; coating for wire used to make electrical motors; potting compound for capacitors; high voltage electrical arresters; filament winding for pressurized rocket fuel tanks and aerospace composites; and a crosslinker for automotive topcoatings.

Examples of UV cured compositions wherein the epoxidized product of the present invention is used as a major ingredient include coating on plastic tubes (for example, tube used for personal care products); coating on steel can ends (for example, vegetable cans); coating on steel containers (for example, biscuit tins and aerosol cans); white base coating used on laminated steel beverage cans; UV inks on film and foil used for packaging; rapid prototyping; and electronic coatings.

The epoxidized product of the present invention may also be used as an acid scavenger composition for example wherein the product is used as an additive present at less than 5 percent of a total composition, including for example an acid scavenger for organophosphate hydraulic fluid; an acid scavenger for poly vinyl chloride (PVC) siding for homes; an acid scavenger for brominated flame retardant composition; and an acid scavenger used in chemical manufacturing processes.

Preferred applications for the curable epoxy resin composition and the cured compound include coatings, inks, potting, and encapsulating compositions.

The present invention will be further illustrated by the following non-limiting examples in comparison with the following comparative examples.

EXAMPLE 1

Toluene, catalyst and 3-cyclohexene-1-carboxylic acid, 3-cyclohexen-1-ylmethyl ester ("Diene 221"), in the amounts described in Table I below, were charged in a 1 liter (L) continuous stirred tube reactor (CSTR) jacketed glass reactor equipped with a mechanical stirrer, thermocouple and reflux condenser.

TABLE I

| COMPONENT | grams |
|---|---|
| Catalyst | 6.621 |
| Diene 221 $C_{14}H_{20}O_2$ | 264.0 |
| $H_2O_2$ as 100 wt percent $H_2O_2$ | 89.77 |
| $H_2O_2$ solution $H_2O_2$ 30.43 wt percent | 295 |
| Toluene | 357.0 |
| Total Amount | 922.62 |

The temperature of the reaction was regulated at a temperature of from 60° C. (for initial 2.5 hours) to about 65° C. (for final 2.5 hours, including cooling time) by setting the temperature of the heating oil which is continuously pumped to the reactor jacket. Considering the exothermicity of the reaction between Diene 221 and $H_2O_2$, a water coil was mounted internally in the reactor in order to control the temperature of the reaction and maintain the temperature fixed at the desiderate value. The reaction is conducted at atmospheric pressure (abut 1 bar) and the magnetic stirrer speed is set at 600 rpm to ensure satisfactory contact between the organic and the aqueous phases.

A mixture of a solution of hydrogen peroxide (30 wt percent concentration) and a buffering agent, as described in Table II below, was charged in a calibrated glass cylinder mounted on an HPLC pump suction side. The glass cylinder is connected to a balance in order to control its flow rate and the time needed to feed the solution into the reactor (60 minutes).

TABLE II

| COMPONENT | Units |
|---|---|
| Buffer solution + $H_2O_2$ solution | 320 g |
| $H_2O_2$ 30.4 wt percent | 295 g |
| $Na_2WO_4 \cdot 2H_2O$ | 2.3751 g |
| $H_3PO_4$ 85 wt percent | 4.10 g |
| NaOH 10 wt percent | 12.6 ml |

The hydrogen peroxide/buffering mixture solution was fed at a feed rate of 4.9 cc/minute with an HPLC pump for 1 hour; and when the feed is stopped (after 60 minutes) and an amount corresponding to 2.2/1 molar ratio respect to the Diene 221 has been added (10 percent $H_2O_2$ excess over stoichiometric ratio), the reaction continues for 4 hours. This 4-hour time period is referred to herein as the "digestion" time.

At the end of the digestion time period, the resulting mixture is cooled down to room temperature (about 25° C.) in 5-10 minutes and discharged into a 1.5 liter separatory funnel, leaving the two separate phases—an organic phase and an aqueous phase.

The two phases were then analyzed and characterized using the analytical methods described as follows:

TABLE III

| Analytical methods and samples | | |
|---|---|---|
| Phase | Analysis | Method |
| Reaction mixture/Organic Phase | Organic phase composition | Gas Chromotography (GC) |
| Reaction mixture/Aqueous Phase | Residual $H_2O_2$ content pH determination | Iodometric Titration Potenziometric |

The product obtained in toluene solution is a mixture of: 3,4-epoxycyclohexylmethyl 3,4-epoxycyclohexanecarboxylate ("ERL4221") and monoepoxy of 3-cyclohexene-1-carboxylic acid, 3-cyclohexen-1-ylmethyl ester ("monoepoxy").

The results of the reaction are described in Table IV below and also summarized in Table VI.

TABLE IV

| COMPONENT | Concentration |
|---|---|
| | (Wt Percent) |
| Diene 221 | 0.00 |
| Monoepoxy | 2.61 |
| ERL-4221 | 43.25 |
| Toluene | 54.39 |
| | (Molar Percent) |
| Diene 221 Conversion | 100.00 |
| (Monoepoxy + ERL4221) Yield | 97.50 |

The ratio between monoepoxy product and monoepoxy product plus ERL4221 product is as described in Table V below:

TABLE V

| COMPONENT | Percent Monoepoxy/ (Monoepoxy + ERL4221) |
|---|---|
| Monoepoxy | 6 |
| ERL-4221 | 94 |

COMPARATIVE EXAMPLE A

Comparative Example A was conducted using the same procedure as described in Example 1 except that no buffer was added to the reaction mixture. The results of this example are shown in Table VI.

EXAMPLE 2

Example 2 was conducted using the same procedure as described in Example 1 except that the reaction time was 2 hours and the aqueous $H_2O_2$ concentration was 15 wt percent, but the same 100 percent base $H_2O_2$ amount was used. The results of this example are shown in Table VI.

COMPARATIVE EXAMPLE B

Comparative Example B was conducted using the same procedure as described in Example 2 except that no buffer was added to the reaction mixture. The results of this example are shown in Table VI.

EXAMPLE 3

Example 3 was conducted using the same procedure as described in Example 1 except that 15 wt percent $H_2O_2$ excess over stoichiometric ratio was used; buffered $H_2O_2$ solution was added in 90 minutes; and the reaction time temperature profile was as follows: initial 2 hours at 60° C., and 3 hours at 65° C. (including cooling time). The results of this example are shown in Table VI.

COMPARATIVE EXAMPLE C

Comparative Example C was conducted using the same procedure as described in Example 3 except that $H_2O_2$ stoichiometric ratio was used. The results of this example are shown in Table VI.

EXAMPLE 4

Example 4 was conducted using the same procedure as described in Example 3, except that reaction time temperature profile was as follows: initial 2 hours at 60° C., 4 hours at 65° C. (including cooling time). The results of this example are shown in Table VI.

The viscosity of each of the cycloaliphatic epoxide samples was measured using a Cannon-Fenske capillary tube from Cannon Instrument Company. The density used to calculate the viscosity of each of the cycloaliphatic epoxide samples was 1.17 g/mL. The viscosity at 25° C. of the cycloaliphatic epoxide of Example 4 was 304 centipoise.

The epoxide equivalent weight of each of the cycloaliphatic epoxide samples was measured using a standard titration method for epoxy resins. The epoxide equivalent weight of the cycloaliphatic epoxide of Example 4 was 132.4 g/equivalent.

In a can end manufacturing operation that uses UV curing, a UV curable coating typically is applied first to tin-free steel sheets (TFS) and the coated sheets are passed through a conveyorized UV cure unit to cure the coating. Next, a thermal-cure sanitary coating, for example, a solvent-based coating, is applied to the opposite side of the sheets. The sheets are then passed through a thermal oven to cure the sanitary coating. A typical cure profile for a sanitary coating can be 204° C. for 10 minutes. The UV coating is therefore exposed to the thermal process used to cure the sanitary coating during can end manufacture. It is prudent to test UV coatings after UV curing and exposing them to a thermal process when it is anticipated the UV coatings will be exposed to a thermal process during a manufacturing process such as can end manufacturing.

Can ends are manufactured by stamping end blanks from coated sheets of steel and forming the blanks into ends. The can ends are attached to can bodies during the packing process after food has been packed into the cans. The ends are attached to the can bodies using a process called double seaming. Double seaming rapidly and severely folds and bends together the edges of the end and the body. The rapid and severe bending of the coated steel requires the coating have a high degree of flexibility and adhesion to withstand the double-seaming process without cracking. After the ends have been double-seamed onto the bodies, the cans of packed food are cooked and sterilized by a process called retort.

TABLE VI

| EXAMPLE | Temp (° C.) | Reaction Time (hours) | $H_2O_2$ (wt percent) | $H_2O_2$ Excess (wt percent) | Buffer Used? | Diene Conversion (percent) | (Monoepoxy + ERL4221) Yield (molar percent) | Percent Monoepoxy/ (Monoepoxy + ERL4221) |
|---|---|---|---|---|---|---|---|---|
| Example 1 | 60/65 | 5 | 30 | 10 | Yes | 100.0 | 97.5 | 6 |
| Comparative Example A | 60/65 | 5 | 30 | 10 | No | 100.0 | 2.0 | 10 |
| Example 2 | 60 | 2 | 15 | 10 | Yes | 97.7 | 80.0 | 22 |
| Comparative Example B | 60 | 2 | 15 | 10 | No | 99.3 | 20.3 | 5 |
| Example 3 | 60/65 | 5 | 30 | 15 | Yes | 99.6 | 98.8 | 7 |
| Comparative Example C | 60/65 | 5 | 30 | 0 | Yes | 99.5 | 99.0 | 13 |
| Example 4 | 60/65 | 6 | 30 | 15 | Yes | 99.6 | 92.5 | 3 |

The results of Examples 1 and 2 and Comparative Examples A and B in Table VI show the effect of a buffer solution and aqueous $H_2O_2$ concentration.

The results of Examples 3 and 4 and Comparative Example C in Table VI show the effect of reaction temperature profile and reaction time on product yield and monoepoxy-ERL4221 ratio.

EXAMPLE 5

In this Example 5, an ultra violet (UV) cured coating was made from the cycloaliphatic epoxide product prepared in Example 4.

Sterilization is required to kill bacteria. Retorting involves placing the cans of food in contact with water or steam or both in a pressure cooker and heating the water above its boiling point, which creates pressure. Cooker conditions for canned food may be 30 minutes to 90 minutes at 121° C. and the pressure may be 14 psi. The exposure to hot water or steam or both during retort places additional stress on the coating on the can ends.

Cycloaliphatic epoxides may be used in UV coatings which are used to coat and protect can ends and other steel packaging products. Tin-free steel sheets used to make food can ends were obtained from Weirton Steel and cut into panels. The UV coating samples were applied onto the TFS panels parallel to the striations on the steel surface and at a thickness of 0.17 mils to 0.22 mils using a number 4 wire-wound rod. The UV coatings were cured using a conveyorized UV unit supplied by Fusion UV Systems, Inc. The UV bulb used was a standard (Fusion "H") 600 W/inch. mercury vapor bulb. The coatings which were tested for flexibility were UV cured using an energy density of about 290 mJ/cm$^2$ which was obtained by operating the conveyor on the UV cure unit at a speed of about 100 feet per minute (fpm). The coatings in Examples 5 and 6 and Comparative Example D were heated in an oven at 204° C. for 10 minutes after UV curing and before testing them for flexibility. The UV coatings in Examples 5 and 6 and Comparative Example D were tested for flexibility using a retort wedge bend test method.

The coated TFS panels were bent and impacted perpendicular to the striations in the steel surface using a wedge-bend instrument in accordance to ATSM D3281-84. The wedge-bent panels were placed in the vapor phase of an autoclave containing deionized water and processed at 121° C. and 14 psi. for about one hour. The length of the crack along the bend after processing was measured and reported as the crack length. Coating flexibility is inversely related to the crack length, that is, a more flexible coating will have a shorter crack length.

UV coating surface-cure rates were measured using a tack-free cotton ball method. The size of the substrate used for the surface-cure rate experiments was 3 inches by 5 inches aluminum foil laminated paper cards supplied by Leneta. Samples used to measure surface-cure rates were prepared by applying the UV coating to the substrate at about 0.2 mils using a number 4 wire-wound bar. The coating surface-cure rate was determined by passing the coated card through the UV unit operated at a given conveyor speed and then placing a cotton ball in contact with the coating surface 2 seconds after the sample exited beneath the UV cure chamber. The coating surface was judged to be cured if cotton fibers did not adhere to it. If cotton fibers adhered to the surface the coating was judged to be tacky or uncured. The conveyor speed was adjusted in increments of 10 fpm and the experiments were repeated until the maximum conveyor speed at which a coating sample was tack-free or cured was determined. The maximum conveyor speed was reported as the surface-cure rate.

Polyols may be added to UV coatings containing cycloaliphatic epoxide to improve the coating flexibility. Hydroxyl groups can react with cycloaliphatic epoxide groups in the presence of the strong acid generated by the cationic photoinitiator during UV cure. The hydroxyl groups can act as chain terminators during the cationic ring-opening polymerization of epoxides. The ratio of cycloaliphatic epoxide to hydroxyl equivalents in a UV coating can be a useful measure of the stoichiometry of these reactive functional groups of the coating. Decreasing the value of the cycloaliphatic epoxide-to-hydroxyl equivalents ratio, which is proportional to increasing the polyol concentration, of the coating will typically increase the coating flexibility. The effect of the ratio on surface-cure rate depends on the ambient relative humidity. At about 50 percent relative humidity, decreasing the value of the cycloaliphatic epoxide-to-hydroxyl equivalents ratio will typically decrease the surface-cure rate. The hydroxyls from the polyol and moisture from the air can combine to contribute to lower surface-cure rate of cationic UV coatings. It is prudent to use a consistent ratio of cycloaliphatic epoxide to hydroxyl equivalents when comparing the effects of different cycloaliphatic epoxy samples on coating flexibility and surface-cure rate.

UNOXOL™ 3,4 Diol was used as the polyol in the UV coating formulations to improve the coating flexibility. The hydroxyl equivalent weight of UNOXOL 3,4 Diol was reported as 72 g/equivalent on the product technical data sheet.

The UV coating formulation used in this Example 5 to measure its flexibility and UV cure rate contained the following ingredients:

| INGREDIENTS | Wt Percent | Equivalents |
|---|---|---|
| Epoxide of Example 4 | 52.5 | 0.396 |
| UNOXOL ™ 3,4 Diol cycloaliphatic diol | 9.5 | 0.132 |
| D.E.R. ™ 331 aromatic epoxy resin | 30 | |
| Cardolite NC-513 reactive diluent | 5 | |
| CYRACURE* UVI-6992 cationic photoinitiator | 2 | |
| Silwet L-7604 polysiloxane surfactant | 1 | |
| Total | 100 | |
| Cycloaliphatic epoxide/hydroxyl equivalents ratio | | 3.0 |

™ Trademark of The Dow Chemical Company ("Dow") or an affiliated company of Dow

The ratio of cycloaliphatic epoxides to hydroxyls was 3.0 for the coating in Example 5. The ambient laboratory temperature and relative humidity were 73° F. and 51 percent, respectively, when the surface-cure rate of Example 5 was measured and when the coating was cured for measuring flexibility.

The retort wedge bend crack length of the coating in Example 5 was 43 mm, which was the average value from five wedge bend samples and the standard deviation was 2.608 mm. The surface-cure rate of the coating in Example 5 was 120 fpm.

EXAMPLE 6

In this Example 6, an UV cured coating was made from the cycloaliphatic epoxide product prepared in Example 3.

The viscosity at 25° C. of the cycloaliphatic epoxide of Example 3 was 250 centipoise. The epoxide equivalent weight of the cycloaliphatic epoxide of Example 3 was 135.5 g/equivalent.

The UV coating formulation used in this Example 6 to measure its flexibility and UV cure rate contained the following ingredients:

| INGREDIENTS | Wt Percent | Equivalents |
|---|---|---|
| Epoxide of Example 3 | 52.7 | 0.39 |
| UNOXOL ™ 3,4 Diol cycloaliphatic diol | 9.3 | 0.13 |
| D.E.R. ™ 331 aromatic epoxy resin | 30 | |
| Cardolite NC-513 reactive diluent | 5 | |
| CYRACURE ™ UVI-6992 cationic photoinitiator | 2 | |
| Silwet L-7604 polysiloxane surfactant | 1 | |
| Total | 100 | |
| Cycloaliphatic epoxide/hydroxyl equivalents ratio | | 3.0 |

™ Trademark of The Dow Chemical Company ("Dow") or an affiliated company of Dow.

The ratio of cycloaliphatic epoxide to hydroxyl equivalents in Example 6 was 3.0, which was the same as Example 5. The ambient laboratory temperature and relative humidity were 73° F. and 51 percent, respectively, when the surface-cure rate of Example 6 was measured and when the coating was cured for measuring flexibility, which was the same as Example 5.

The retort wedge bend crack length of the coating in Example 6 was 39 mm, which was the average value from five wedge bend samples and the standard deviation was 2.168 mm. The surface-cure rate of the coating in Example 6 was 110 fpm.

The flexibility results for Examples 5 and 6 were very similar to one another and the reported difference in flexibility between the two samples (3.4 mm) is probably not significant. The results demonstrate good flexibility for the coating formulations described in Examples 5 and 6. The surface-cure rates for Examples 5 and 6 were very similar and the reported difference (10 fpm) is probably not significant. The results demonstrate a good cure rate for the coating formulations 5 and 6. The coatings of Examples 5 and 6 performed very similarly, with regard to flexibility, to a coating made from a commercially available resin, "UVR-6107", commercially available from The Dow Chemical Company, which is described in Comparative Example D.

COMPARATIVE EXAMPLE D

The epoxide equivalent weight of the cycloaliphatic epoxide of Comparative Example D was 136.1 g/equivalent.

The UV coating formulation used in this Comparative Example D to measure its flexibility and UV cure rate contained the following ingredients:

| INGREDIENTS | Wt. Percent | Equivalents |
| --- | --- | --- |
| CYRACURE ™ UVR-6107 cycloaliphatic epoxide resin | 52.7 | 0.39 |
| UNOXOL ™ 3,4 Diol cycloaliphatic diol | 9.3 | 0.13 |
| D.E.R. ™ 331 aromatic epoxy resin | 30 | |
| Cardolite NC-513 reactive diluent | 5 | |
| CYRACURE ™ UVI-6992 cationic photoinitiator | 2 | |
| Silwet L-7604 polysiloxane surfactant | 1 | |
| Total | 100 | |
| Cycloaliphatic epoxide/hydroxyl equivalents ratio | | 3.0 |

™ Trademark of The Dow Chemical Company ("Dow") or an affiliated company of Dow

The ratio of cycloaliphatic epoxide to hydroxyl equivalents in Comparative Example D was 3.0, which was the same as Example 5 and Example 6. The ambient laboratory temperature and relative humidity were 73° F. and 51 percent, respectively, when the surface-cure rate of Comparative Example D was measured and when the coating was cured for measuring flexibility, which was the same as Example 5 and Example 6.

The retort wedge bend crack length of the coating in Comparative Example D was 38 mm, which was the average value from five wedge bend samples and the standard deviation was 2.191 mm. The surface-cure rate of the coating in Comparative Example D was 120 fpm.

What is claimed is:
1. A process for producing an epoxidized product comprising
(a) mixing:
(i) an olefin containing two or more double bonds;
(ii) a transition metal catalyst; and
(iii) a solvent; and
(b) metering in, over a pre-determined period of time and at a regulated pre-determined first reaction temperature at a pH of less than about 5, a solution of:
(i) an excess of an aqueous hydrogen peroxide oxidant over the stoichiometric ratio of the hydrogen peroxide oxidant to the olefin; and
(ii) a buffering agent; and
(c) increasing the first reaction temperature by at least about 5 degrees C. to a second reaction temperature and continuing the reaction for a pre-determined period of time at said second reaction temperature to form an epoxidized product;
wherein the epoxidized product resulting from the reaction has an epoxide yield of greater than about 90% by weight of the total epoxidized product, a selectivity of greater than about 90% by weight of the total epoxidized product, a % monoepoxide of less than about 10% by weight of the total epoxidized product, and an OH-terminated by-products content of less than about 8% by weight of the total epoxidized product.

2. The process of claim 1 wherein the first and second reaction temperatures are within a range of from 10° C. to 100° C.

3. The process of claim 1 wherein the catalyst comprises a catalyst illustrated by the following chemical structure:

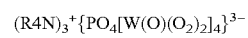

where R is a C1-C24 hydrocarbon chain.

4. The process of claim 1 wherein the buffering agent comprises a mixture of (a) a tungstate material to assist in maintaining the activity of the catalyst; (b) a phosphoric acid also to assist in maintaining the activity of the catalyst; and (c) an alkali metal salt to maintain the pH of the reaction mixture.

5. The process of claim 1 wherein the solvent is selected from the group comprising alkyl esters, halogenated hydrocarbons, cycloaliphatic hydrocarbons, aromatic hydrocarbons, alcohols and mixtures thereof.

6. The process of claim 1 wherein the first reaction temperature is in the range of −10° C. to 100° C., and said metering occurs over a period of from 1 minute to 300 minutes.

7. The process of claim 1 wherein the olefin comprises a diene compound.

8. An epoxidized product prepared by the process of claim 7.

9. A coating comprising a cured epoxy resin obtained by curing a curable coating composition comprising (a) the epoxidized product of claim 8, and (b) a curing agent.

10. The process of claim 7 wherein the diene compound comprises a cyclic diene compound.

11. An epoxidized product prepared by the process of claim 10.

12. The process of claim 10 wherein the cyclic diene compound comprises a compound having the following formula:

FORMULA IA

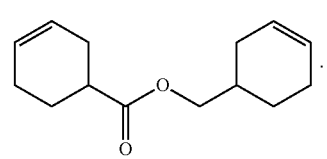

13. An epoxidized product prepared by the process of claim 12.

14. The epoxidized product of claim 13 containing less than about 8 percent by weight of the following oligomeric structure:

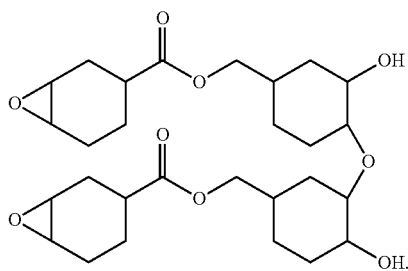

15. The process of claim 12 wherein the epoxidized product comprises an epoxy compound having the following formula:

FORMULA IB

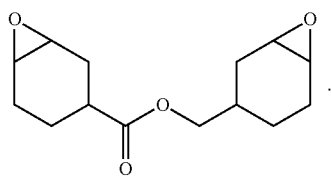

16. An epoxidized product prepared by the process of claim 15.

17. The epoxidized product of claim 16 containing less than about 8 percent by weight of the following oligomeric structure:

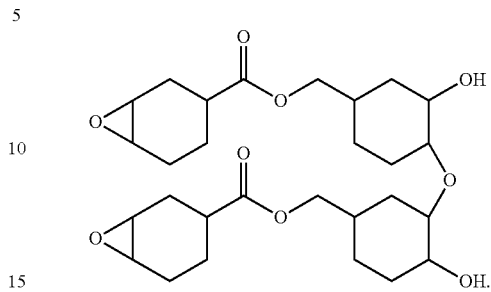

18. An epoxidized product prepared by the process of claim 1.

19. A process of preparing a curable epoxy resin composition comprising mixing the epoxidized product of claim 18 and a curing agent.

20. A curable epoxy resin composition comprising the epoxidized product of claim 18 and a curing agent.

21. A cured epoxy resin obtained by curing the curable epoxy resin composition of claim 20.

* * * * *